United States Patent [19]

Poist

[11] 4,152,357
[45] May 1, 1979

[54] PLATINUM-TIN HYDROFORMYLATION CATALYST

[75] Inventor: John E. Poist, High Bridge, N.J.

[73] Assignee: Celanese Corporation, New York, N.Y.

[21] Appl. No.: 853,834

[22] Filed: Nov. 22, 1977

Related U.S. Application Data

[62] Division of Ser. No. 794,781, May 9, 1977, Pat. No. 4,101,564.

[51] Int. Cl.² .............................................. C07C 45/08
[52] U.S. Cl. ............................................. 260/604 HF
[58] Field of Search ................. 260/604 HF, 632 HF; 568/909

[56] References Cited
U.S. PATENT DOCUMENTS

| | | | |
|---|---|---|---|
| 3,501,531 | 3/1970 | Wilkinson | 260/604 HF |
| 3,832,391 | 8/1974 | Parshall | 260/604 HF |
| 3,876,672 | 4/1975 | Mrowca | 260/410.9 R |
| 3,981,925 | 9/1976 | Schwager et al. | 260/604 HF |
| 3,996,293 | 12/1976 | Knifton | 260/604 HF |
| 4,013,584 | 3/1977 | Knifton | 260/604 HF |

Primary Examiner—Werren B. Lone

[57] ABSTRACT

This invention provides a novel hydroformylation catalyst which is an ionic combination of a quaternary ammonium component and a ligand stabilized complex of platinum dihalide and stannous halide.

A preferred species of the invention hydroformylation catalyst can be represented empirically by the chemical structure:

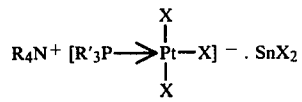

wherein R and R' are organic radicals such as alkyl and aryl, and X is a halogen radical.

The present invention stabilized platinum-tin complex hydroformylation catalyst provides a faster reaction rate at lower pressures and a superior combination of a high level of olefin conversion and efficiency to aldehyde products than prior art hydroformylation catalysts.

5 Claims, No Drawings

PLATINUM-TIN HYDROFORMYLATION CATALYST

This is a division of application Ser. No. 794,781 filed May 9, 1977, now U.S. Pat. No. 4,101,564.

BACKGROUND OF THE INVENTION

The hydroformylation reaction is employed on a commercial scale to prepare straight chain and branched chain mixtures of aldehydes and alcohols from olefinically unsaturated hydrocarbons.

For reasons of economic feasibility, improvements in hydroformylation catalysts and procedures are being investigated to achieve increased hydroformylation reaction rates and conversions, and increased selectivity to specific hydroformylation products.

The selective production of straight chain aldehydes and alcohols is particularly desirable. Higher oxo alcohols have become important intermediates for synthesis of biodegradable surface-active agents. Oxo alcohols are highly biodegradable, but the biodegradability is inversely proportional to the proportion of branched chain isomer present in an oxo alcohol mixture. There is continuing development effort to increase alpha-olefin hydroformylation selectivity to linear paraffinic aldehydes and alcohols.

Cobalt carbonyl is a conventional catalyst employed for hydroformylation reaction, but large quantities of branched chain aldehydes are produced with this catalyst. Rhodium carbonyl complexes containing tertiary phosphine or phosphite ligands [Evans et al, J. Chem. Soc. A, 3133 (1968); Pruett and Smith, J. Org. Chem., 34, 327 (1969)] are useful at low pressures and give higher ratios of straight chain to be branched chain products. Similar cobalt carbonyl complexes [Slaugh and Mullineaux, J. Organometal. Chem., 13, 469 (1968)] also give more straight chain product, but produce alcohols as the primary products.

More recently developed hydroformylation catalysts and processes achieve some improved selectivity to linear products but still result in a high yield of branched chain aldehyde and alcohol products, and the reaction rate and level of olefin feed conversion is not sufficiently high. Illustrative of recent advances in hydroformylation technology are U.S. Pat. Nos. 3,488,296; 3,652,676; 3,876,672; 3,981,925; and 3,984,486.

U.S. Pat. No. 3,981,925 is particularly pertinent with respect to improved hydroformylation selectivity. The said patent discloses a process for hydroformylation of olefins to aldehydes in the presence of a ligand stabilized platinum halide complex in combination with a Group IVA metal halide. The hydroformylation selectivity of the U.S. Pat. No. 3,981,925 process favors formation of straight chain aldehye, e.g., in Example 1 the mole ratio of 1-octylaldehyde to 2-methylheptaldehyde product from heptene-1 hydroformylation is 9:1. However, also produced are 2.7 mole percent of heptene-2 and heptene-3 isomerization products and 8.7 mole percent of high boiling products. Further, the reaction rate and the efficiency of olefin conversion to aldehydes are lower than desirable, and a high pressure of carbon monoxide is required to suppress olefin isomerization.

There remains a need for hydroformylation catalysts and processes which provide for olefin conversion to aldehyde products at a fast reaction rate at lower pressures and with improved efficiency and selectivity, and with a concomitant reduction in the yield of isomerization, hydrogenation, and polymerization products.

Accordingly, it is a main object of this invention to provide a novel hydroformylation catalyst which promotes the conversion of olefins to aldehydes with a high rate of reaction and a high level of conversion at low carbon monoxide pressures.

It is a further object of this invention to provide an improved hydroformylation process for rapid conversion of alpha-olefins to linear aldehydes with high efficiency and selectivity.

Other objects and advantages of the present invention shall become apparent from the accompanying description and examples.

DESCRIPTION OF THE INVENTION

One or more objects of the present invention are accomplished by the provision of a hydroformylation process for converting olefins to aldehydes with a high reaction rate and a high conversion efficiency which comprises contacting an olefin with hydrogen and carbon monoxide at a temperature between about 25° C. and 125° C. and a pressure between about 100 and 3000 psi in the presence of a stabilized platinum-tin complex hydroformylation catalyst which corresponds to the formula:

$$R_4M^+[L{\rightarrow}PtX_3]^-\cdot SnX_2$$

wherein X is a halogen radical selected from chlorine, bromine and iodine; M is a Group VA element selected from nitrogen, phosphorus and arsenic; R is a radical selected from hydrogen and aliphatic and aromatic groups containing between one and about twenty carbon atoms; and L is a ligand having the formula:

$$R'_3M'$$

wherein R' is an organic radical selected from alkyl, alkoxy, aryl and aryloxy groups containing between one and about twenty carbon atoms, and M' is a Group VA element selected from phosphorus, arsenic, antimony and bismuth.

The invention process is contemplated for hydroformylation of olefins containing between about 2 and 30 carbon atoms. The term olefin is meant to include substituted olefinically unsaturated compounds such as styrene. The invention process provides particular advantages in the hydroformylation of linear alkene-1 hydrocarbons containing between about 3 and 20 carbon atoms. Illustrative of linear alkene-1 compounds are propene-1, butene-1, pentene-1, hexene-1, heptene-1, decene-1, undecene-1, eicosene-1, and the like.

Hydroformylation Catalyst

A preferred catalyst for the practice of the invention hydroformylation process nominally can be represented by the structural formula:

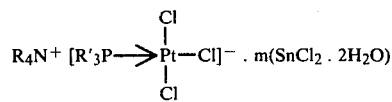

wherein R is a radical selected from hydrogen and alkyl and aryl groups containing between one and about twenty carbon atoms; and R' is an organic radical selected from alkyl, alkoxy, aryl and aryloxy groups containing between one and about twenty carbon atoms; and m is an integer between one and about ten.

The catalyst can be employed in a quantity which is in a molar ratio of about one mole of catalyst per 20-1000 moles of olefin feed being hydroformylated. An average molar ratio of 1 mole of catalyst per 100-500 moles of olefin is generally a preferred range.

An important aspect of a present invention hydroformylation system is the relative quantities of catalyst components provided in the hydroformylation medium.

The stannous halide component is provided in a molar ratio between about 1-50 moles, and preferably between about 1-10 moles, per mole of platinum dihalide component in the hydroformylation medium. A highly preferred stannous halide component is stannous chloride dihydrate. The dihydrate form of stannous chloride promotes a faster olefin hydroformylation reaction rate and a higher level of olefin conversion than does anhydrous stannous chloride.

The ligand component is complexed with the platinum dihalide component of the catalyst in a molar ratio of 1:1 with respect to the platinum dihalide content of the catalyst complex. In one embodiment of the present invention, the ligand is incorporated in the hydroformylation medium in a molar excess, i.e., a quantity of ligand which is in molar excess over that required to complex and stabilize the platinum dihalide component of the catalyst system.

The presence of excess ligand in the olefin hydroformylation system promotes selective production of straight chain aldehydes from alpha-olefins. The excess ligand can be the same or different than the ligand present in the ligand stabilized platinum-tin complex. The quantity of excess ligand can average in the range between about 1-100 moles per mole of platinum dihalide in the hydroformylation catalyst system.

Illustrative of suitable catalyst ligands are the following compounds:

| | |
|---|---|
| $P(C_6H_5)_3$ | $P(CH_3)(n\text{-}C_4H_9)_2$ |
| $P(CH_3C_6H_4)_3$ | $P(n\text{-}C_4H_9)_3$ |
| $Sb(C_6H_5)_3$ | $Sb(n\text{-}C_4H_9)_3$ |
| $As(C_6H_5)_3$ | $As(n\text{-}C_4H_9)_3$ |
| $P(Cl)(C_6H_5)_2$ | $Bi(n\text{-}C_4H_9)_3$ |
| $P(OC_6H_5)_3$ | $P(CH_3)_2(C_6H_5)$ |
| $Bi(C_6H_5)_3$ | $P(OC_4H_9)_3$ |
| $P(O)(C_6H_5)_3$ | $P(O)(n\text{-}C_4H_9)_3$ |

Hereinabove, the general formula for the invention catalyst is represented by the chemical structure:

$$R_4M^+[L{\rightarrow}PtX_3]^-\cdot SnX_2$$

In the quarternary ionic moiety (i.e., $R_4M^+$), M is a Group VA element selected from nitrogen, phosphorus and arsenic. During the preparation of an invention catalyst system, the quarternary component of the hydroformylation catalyst is introduced conveniently in the form of a quarternary halide salt:

$$R_4M^+X$$

The R substituent is either hydrogen or a group selected from aliphatic and aromatic organic radicals such as alkyl, aryl, and the like. The R substituents can be similar or different in the quarternary halide compound. Illustrative of R substituents are hydrogen, methyl, ethyl, chloroethyl, ethoxyethyl, butyl, heptyl, decyl, cyclohexyl, phenyl, chlorophenyl, tolyl, phenylethyl, and the like.

Hydroformylation Conditions

As a general procedure, the catalyst system is first formed by admixture of the catalyst components in a deoxygenated solvent medium in a hydroformylation reaction zone. Excess ligand can perform as the solvent medium. The hydroformylation zone is pressured with hydrogen and carbon monoxide and heated to a selected reaction temperature. Olefin feed is then charged to the hydroformylation zone, and the reaction is conducted until the desired conversion level and efficiency have been attained.

It is preferred that the temperature of the hydroformylation reaction be maintained in the range between about 25° C. and 125° C. For most of the olefin oxonation reactions, a reaction temperature between about 50° C. and 110° C. and a reaction time between about 2 and 5 hours are particularly preferred.

The pressure in the hydroformylation reaction zone can vary over a range between about 50-3000 psi. Preferred pressures are those in the range between about 100-1500 psi, particularly for the selective hydroformylation of alpha-olefins to linear aldehydes.

The ratio of hydrogen to carbon monoxide can vary broadly over a mole ratio range between about 30:1 and 1:30. The average mole ratio will vary between about 10:1 and 1:10. The quantity of hydrogen/carbon monoxide charged should be at least sufficient to satisfy the stoichiometric requirements of the olefin hydroformylation system.

Although it is not essential, a inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including orthodichlorobenzene; ethers such as tetrahydrofuran, dimethoxyethane and dioxane; halogenated paraffins including methylene chloride; paraffinic hydrocarbons such as heptane; and the like.

The present invention olefin hydroformylation process is characterized by a faster hydroformylation reaction rate and a superior combination of a high level of olefin conversion and efficiency to aldehyde products than prior art processes employing a platinum catalyst. Hence, in EXAMPLE I of the present disclosure in accordance with the hydroformylation procedure and catalyst of U.S. Pat. No. 3,981,925, 84 percent of the olefin feed converted to 95 mole percent of aldehydes in 180 minutes at 1500 psig. In EXAMPLE III in accordance with the present invention process, 82 percent of the olefin feed converted to 94 mole percent of aldehydes in 56 minutes at 500 psig.

The following examples are illustrative of specific embodiments of the present invention process. As it is apparent to those skilled in the art, in the light of the foregoing disclosure numerous modifications are possible in the practice of the invention process without departing from the scope or concept thereof.

EXAMPLE I

This Example illustrates the hydroformylation of hexene-1 in the presence of a prior art platinum catalyst complex.

In a manner similar to that described in U.S. Pat. No. 3,981,925, to a 300 milliliter magnadrive autoclave was added a solution of 58.5 milliliters of methyl isobutyl ketone and 0.325 gram of stannous chloride dihydrate under a nitrogen atmosphere. After 15 minutes, 0.229 gram of bis(triphenylphosphine)-platinum dichloride complex was added with stirring.

The autoclave was pressured with 1500 psig $H_2/CO$ (1:1) and heated to 78° C. A solution of 4.88 milliliters of hexene-1 and 2.9 milliliters of benzene were charged to the autoclave, and the hydroformylation was commenced.

The hydroformylation reaction as conducted at 78°–80° C. for 180 minutes. The reactor was cooled, and the contents were analyzed by gas chromatography. The analytical data indicated that 84 percent of the hexene-1 feed had converted to 95 mole percent of heptanal-1 and 2-methylhexanal-1. The aldehyde molar ratio of heptanal-1 to 2-methylhexanal-1 was 11.4 to 1.

EXAMPLE II

This Example illustrates the hydroformylation of hexene-1 in the presence of a present invention hydroformylation catalyst.

In a manner similar to that described in EXAMPLE I, an autoclave was charged with 52 milliliters of methyl ethyl ketone and 0.325 gram of stannous chloride dihydrate, and then with 0.030 gram of tetramethyl ammonium chloride, and 0.136 gram of tri(n-butyl)phosphine stabilized platinum chloride:

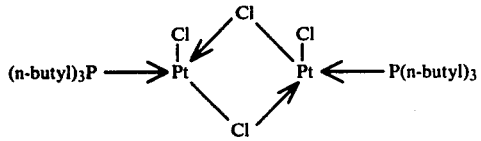

The highly reactive catalyst complex which formed corresponded to the empirical formula:

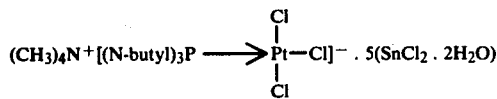

The autoclave was pressured with 500 psig $H_2/CO$ (1:1) and heated to 78° C. A solution of 4.88 milliliters of hexene-1 and 0.88 milliliters of benzene were charged to the autoclave, and the hydroformylation reaction was conducted at 78°–80° C. for 106 minutes.

The reactor was cooled, and analytical data indicated that 77.7 percent of the hexene-1 had converted to 93 mole percent of heptanal-1 and 2-methylhexanal. The aldehyde molar ratio of heptanal-1 to 2-methylhexanal-1 was 7.1:1.

EXAMPLE III

This Example is a further illustration of the hydroformylation of hexene-1 in the presence of a present invention hydroformylation catalyst.

In a manner similar to that described in EXAMPLE I, an autoclave was charged with 52 milliliters of methyl ethyl ketone and 0.325 gram stannous chloride dihydrate, and then with 0.107 gram of tetra-n-butyl ammonium iodide and 0.136 gram of tri(n-butyl)phosphine stabilized platinum chloride.

The autoclave was pressured with 500 psig $H_2/CO$ (1:1) and heated to 80° C. A solution of 4.88 milliliters of hexene-1 and 0.88 milliliters of benzene were charged to the autoclave, and the hydroformylation reaction was conducted at 80°–82° C. for 56 minutes.

The reactor was cooled, and analytical data indicated that 82 percent of the hexene-1 had converted to 94 mole percent of heptanal-1 and 2-methylhexanal. The aldehyde molar ratio of heptanal-1 to 2-methylhexanal-1 was 9:1.

EXAMPLE IV

In a manner similar to that described in EXAMPLE I, an autoclave was charged with 0.325 gram stannous chloride dihydrate, 0.136 gram of tri(n-butyl) phosphine stabilized platinum dichloride and 0.030 gram of tetramethyl ammonium chloride.

The autoclave was pressured with 100 psig $H_2/CO$ (1:1), and hexene-1 was hydroformylated at a temperature of 78°–80° C. for 235 minutes. The conversion of hexene-1 was 65 percent to a 76 percent yield of heptanal-1 and 2-methylhexanal in a normal/iso ratio 8.9:1. The remaining 24 percent of the conversion product mixture was composed of isomerization derivatives.

What is claimed is:

1. A process for the preparation of alkanal-1 by hydroformylation of an alpha-olefin with a high reaction rate and a high molar conversion and efficiency which comprises contacting an alpha-olefin with hydrogen and carbon monoxide at a temperature between about 25° C. and 125° C. and a pressure between about 50 and 3000 psi in the presence of a hydroformylation catalyst corresponding to the formula:

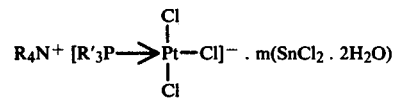

wherein R is a radical selected from hydrogen and alkyl and aryl groups containing between one and about twenty carbon atoms; R' is an organic radical selected from alky, alkoxy, aryl and aryloxy groups containing between one and about twenty carbon atoms; and m is a integer between one and about ten.

2. A hydroformylation process in accordance with claim 1 wherein R' is phenyl in the formula.

3. A hydroformylation process in accordance with claim 1 wherein R' is butyl in the formula.

4. A hydroformylation process in accordance with claim 1 wherein R is hydrogen in the formula.

5. A hydroformylation process in accordance with claim 1 wherein R is methyl in the formula.

* * * * *